US011357900B2

United States Patent
Schlinker et al.

(10) Patent No.: US 11,357,900 B2
(45) Date of Patent: Jun. 14, 2022

(54) SYSTEMS AND METHODS FOR PRIMING A FLUID CIRCUIT

(71) Applicant: Fenwal, Inc., Lake Zurich, IL (US)

(72) Inventors: Alaina Schlinker, Chicago, IL (US); Steven Binninger, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/600,447

(22) Filed: May 19, 2017

(65) Prior Publication Data

US 2017/0340799 A1    Nov. 30, 2017

Related U.S. Application Data

(60) Provisional application No. 62/342,757, filed on May 27, 2016.

(51) Int. Cl.
| | | |
|---|---|---|
| *A61M 1/34* | (2006.01) | |
| *A61M 1/26* | (2006.01) | |
| *A61M 1/36* | (2006.01) | |
| *A61M 1/02* | (2006.01) | |

(52) U.S. Cl.
CPC .......... *A61M 1/3644* (2014.02); *A61M 1/025* (2013.01); *A61M 1/0209* (2013.01); *A61M 1/0272* (2013.01); *A61M 1/0281* (2013.01); *A61M 1/3496* (2013.01); *A61M 1/265* (2014.02); *A61M 2205/3331* (2013.01); *A61M 2205/3393* (2013.01)

(58) Field of Classification Search
CPC .............. A61M 1/3644; A61M 1/0281; A61M 1/0272; A61M 1/3496; A61M 1/025; A61M 1/0209; A61M 1/265; A61M 1/3621; A61M 1/3643; A61M 2205/3331; A61M 2205/3393; A61M 2205/33; A61M 2205/3334; A61M 2205/3379
USPC ........................ 210/96.2, 138–140, 143, 645
See application file for complete search history.

(56) References Cited

U.S. PATENT DOCUMENTS

| | | | |
|---|---|---|---|
| 4,721,564 A * | 1/1988 | Harada .................. | A61M 1/342 210/321.72 |
| 5,053,121 A | 10/1991 | Schoendorfer et al. | |
| 5,194,145 A | 3/1993 | Schoendorfer | |
| 8,562,908 B2 * | 10/2013 | Kenley .................. | A61L 2/186 422/44 |
| 2013/0334420 A1 | 12/2013 | Min et al. | |
| 2014/0357465 A1 * | 12/2014 | Barry, Jr. et al. | |

(Continued)

FOREIGN PATENT DOCUMENTS

| | | |
|---|---|---|
| EP | 3192541 | 7/2017 |
| WO | WO-9312430 A1 * | 6/1993 |
| WO | WO 2012125457 | 9/2012 |

(Continued)

OTHER PUBLICATIONS

European Search Report from the European Patent Office dated Oct. 18, 2017 for European Patent Application No. 17171302.7.

*Primary Examiner* — Nam X Nguyen
*Assistant Examiner* — Julia L. Wun
(74) *Attorney, Agent, or Firm* — Cook Alex Ltd.

(57) ABSTRACT

Methods and systems for priming a disposable fluid circuit for the processing of a biological fluid are disclosed. The methods and systems allow for variable and configurable priming of the flow path(s) leading to one or more biological fluid source containers.

13 Claims, 5 Drawing Sheets

(56) References Cited

U.S. PATENT DOCUMENTS

2016/0177262 A1  6/2016  Wegener et al.

FOREIGN PATENT DOCUMENTS

| WO | WO 2012125470 | 9/2012 |
| WO | WO 2013043433 | 3/2013 |

* cited by examiner

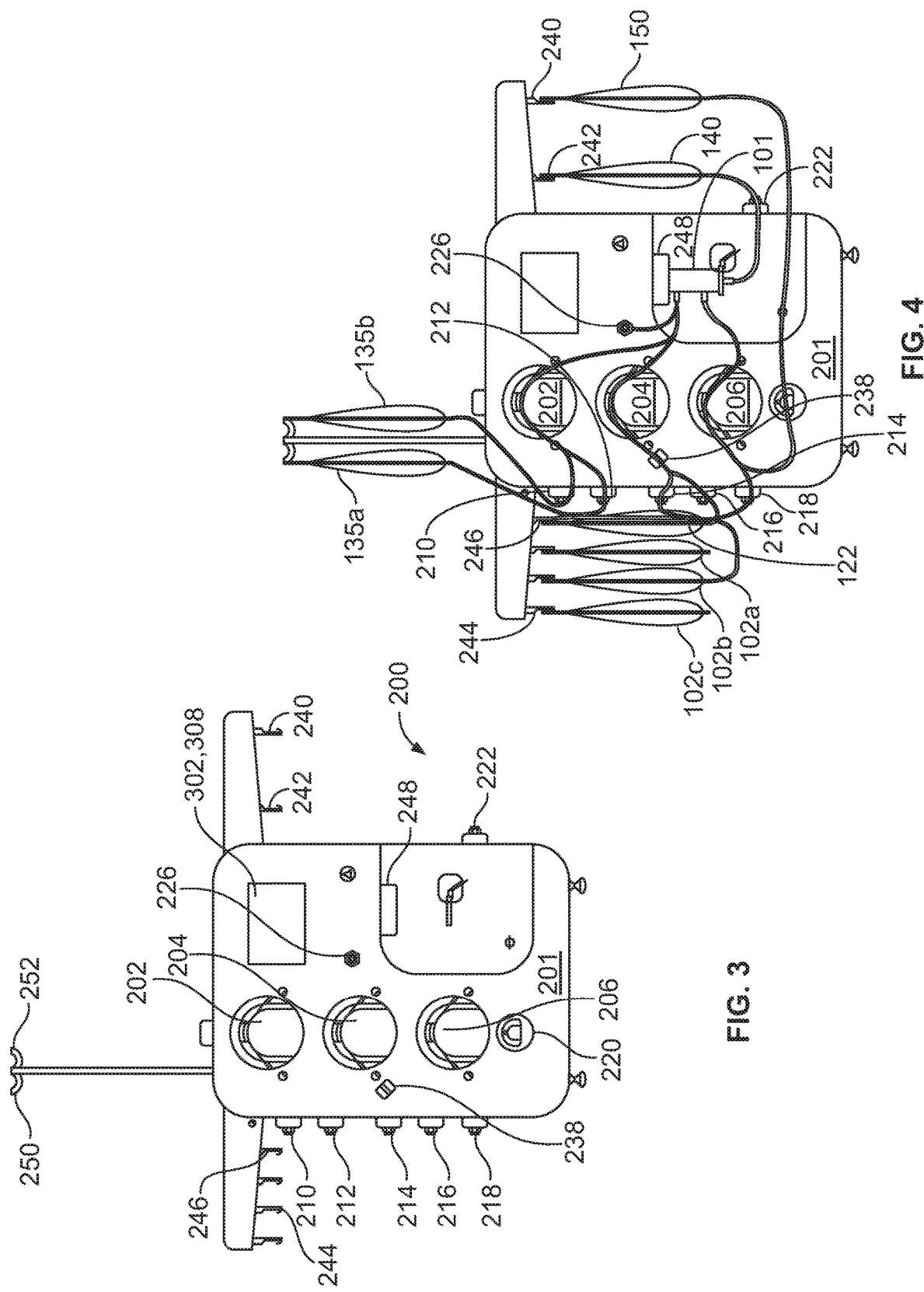

SYSTEMS AND METHODS FOR PRIMING A FLUID CIRCUIT

CROSS-REFERENCE TO RELATED APPLICATION

This application claims the benefit of and priority to U.S. Provisional Patent Application Ser. No. 62/342,757, filed on May 27, 2016, the disclosure of which is incorporated herein by reference in its entirety.

FIELD OF THE DISCLOSURE

The present disclosure is directed to the processing of biological fluids, such as suspensions of biological cells, blood and/or blood components, using a disposable fluid circuit. More particularly, the present disclosure is directed to methods and systems for priming the fluid circuit prior to the processing of the biological fluid. Even more particularly, the present disclosure is directed to methods and systems for configuring the priming of the fluid circuit in a particular manner where a single source container or multiple source containers of the biological fluid are to be processed. Parameters of the desired priming can be entered by the operator and the priming subsequently carried out by the system with minimal operator intervention.

BACKGROUND

Biological cells may be processed for a variety of reasons. For example, blood cells previously collected may be washed and/or concentrated for subsequent use as part of a therapy. The processing of biological fluids such as biological cells, blood or blood components typically involves using a reusable processing apparatus ("hardware") and a disposable fluid circuit adapted for mounting or other association with the hardware. The fluid circuit typically includes, among other things, a separation device, (plastic) containers and associated tubing that defines a flow path through the circuit.

Prior to processing the biological fluid, the fluid circuit is "primed" by introducing a liquid priming solution into the circuit to remove air that may reside within the flow paths of the circuit. Where one or more containers of the biological fluid serve as the source of biological fluid, priming may include introducing priming solution to the source lines in fluid communication with the source container(s) and to the other containers and tubing on the kit, resulting in some mixing of the priming solution with the biological fluid within the source container. To avoid "shocking" the biological cells with a sudden change in osmolarity caused by the mixing of the priming solution with the cells, it may be desirable to allow for a time period of "osmolarity balancing" to occur. This may be particularly challenging to achieve where multiple containers of source fluid are provided. Thus, a system that can be configured to effectively and automatically prime the source lines of the fluid circuit without "shocking" the cells and tailor the priming steps to the volume and type of biological fluid and to the number of containers of biological fluid and container capacity would be desirable.

SUMMARY

In one aspect, the subject matter of the present disclosure is directed to a method for priming at least a portion of a fluid circuit of a biological fluid processing system. The method includes, pumping a priming solution from one or more containers of priming solution through a portion of said fluid circuit and delivering a selected volume of priming solution through a source line of the fluid circuit to a source container of the biological fluid. The method may also allow for pausing the delivery of the priming solution for a selected period of time, mixing the priming solution with the biological fluid in the source container and delivering a selected volume of priming solution to a source line of the fluid circuit after pausing for the selected period of time. The source line may be a source line leading to a single container of source fluid or a source line of one of a plurality of containers of source fluid.

In another aspect, the subject matter of the present disclosure is directed to an automated system for the processing of biological fluid. The system includes a reusable hardware unit with a separation device drive unit for receiving a separation device and a plurality of pumps. The system further includes a disposable fluid circuit mountable on the reusable hardware unit. The disposable fluid circuit includes tubing defining a flow path between one or more containers of priming solution and one or more source containers of a biological fluid. Still further, the system includes a controller configured to control the delivery of the priming solution to a source line communicating with the source container. The controller effects the opening and closing of clamps to control flow through the circuit, effects rotation of the pumps, thereby effecting the delivery of priming solution to the source lines and the source containers, in accordance with instructions and/or input provided by the operator.

BRIEF DESCRIPTION OF THE DRAWINGS

FIG. 3 is an enlarged view of the front panel of the reusable processing apparatus;

FIG. 4 is another view of the front panel of a reusable processing and/or cell washing apparatus with a disposable fluid circuit mounted thereon;

DETAILED DESCRIPTION OF THE EMBODIMENTS

The methods and systems disclosed herein typically employ a reusable separation apparatus and one or more disposable fluid circuits adapted for association with the reusable apparatus. The reusable separation apparatus may be any apparatus that can provide for the automated processing of biological cells, as well as automated preparation, such as priming, of the system prior to the processing of cells. By "automated," it is meant that the apparatus can be pre-programmed to carry out the system priming and cell processing steps without substantial operator involvement. Of course, even in the automated system of the present disclosure, it will be understood that some operator involvement will be required, including the loading or mounting of the disposable fluid circuits onto the reusable apparatus and entering certain processing parameters. Additional manual steps may be required as well. However, the reusable apparatus can be programmed to perform the processing of the biological cells through the disposable circuit(s) described below without substantial operator intervention.

Examples of a reusable apparatus include the Aurora® Plasmapheresis System and the Lovo Cell Processing System, both sold by Fenwal, Inc., a Fresenius Kabi Company, of Lake Zurich, Ill. Both the Aurora® Plasmapheresis System and the Lovo Cell Processing System are compact cell processors for washing and concentrating biological fluid such as certain blood cell components. The Lovo Cell Processing System uses a spinning membrane separator. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which is also incorporated herein in its entirety. In addition, systems and methods that utilize a spinning porous membrane are also disclosed in U.S. Provisional Patent Application No. 61/537,856, filed on Sep. 22, 2011, International (PCT) Application No. PCT/US2012/028522, filed Mar. 9, 2012, International (PCT) Application No. PCT/US2012/054859, filed Sep. 12, 2012, and U.S. patent application Ser. No. 14/574,539, filed Dec. 18, 2014, the contents of each are incorporated herein by reference. The references identified above describe a membrane covered spinner having an interior collection system disposed within a stationary shell.

It will be appreciated that a reusable apparatus utilizing a principle of separation other than a spinning membrane, such as centrifugation, but still requiring a disposable fluid circuit may also be used in the methods and systems described herein.

Figure 1:
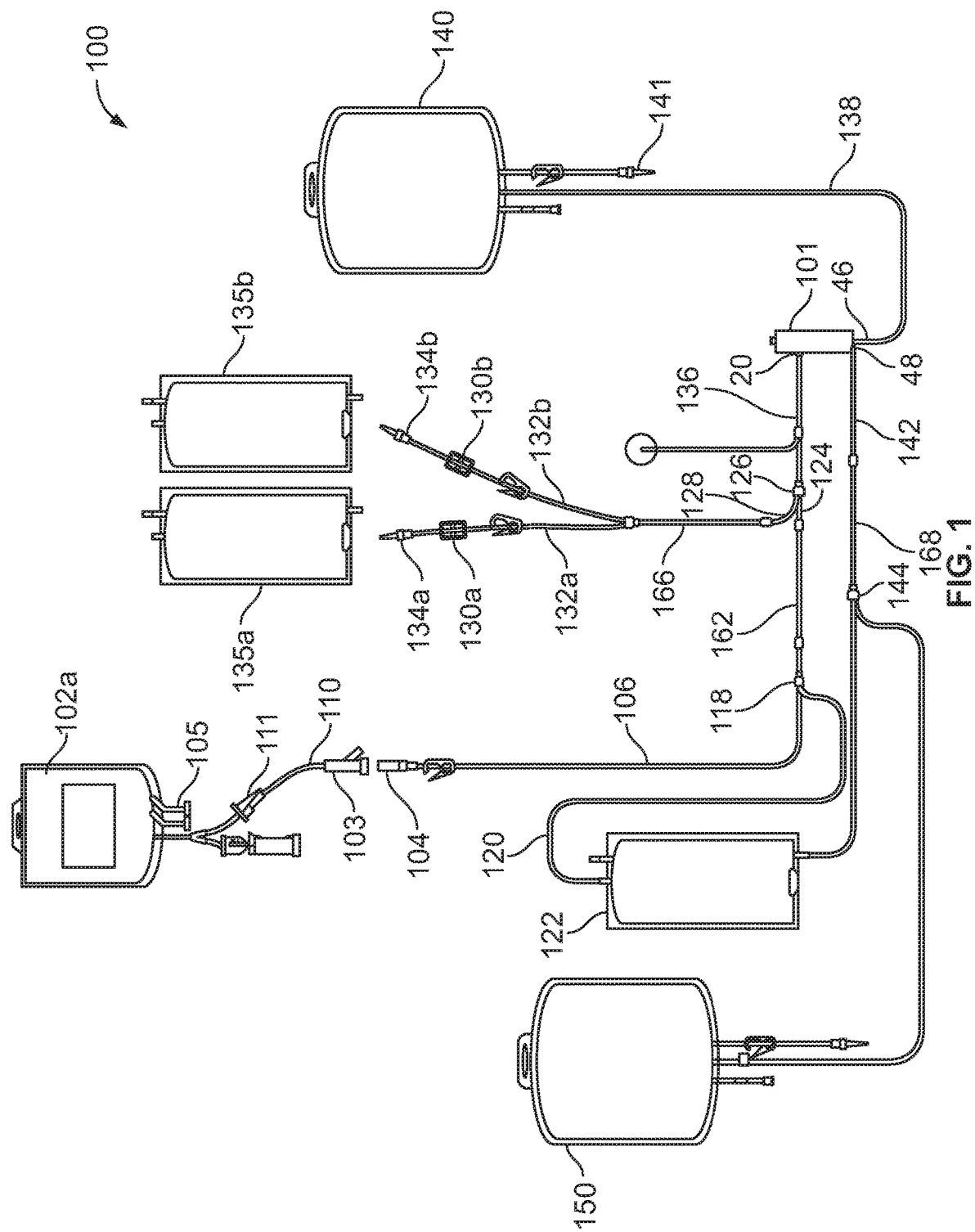
FIG. 1 is a schematic view of one embodiment of a disposable fluid circuit for use in the systems and methods described herein.

Turning first to FIG. 1, the systems described herein preferably include a disposable fluid circuit for use in the processing of the biological fluid (e.g., suspension of biological cells). Fluid circuit 100 is adapted for mounting onto a reusable hardware component, described below. Circuit 100 may include an integrated separation device, such as, but not limited to, the spinning membrane 101 described herein. Circuit 100 may also include filtrate bag or container 140, retentate container or bag 150, and in-process container 122. Disposable fluid circuits of the type described below may further include sampling assemblies (not shown) for collecting samples of biological cells, "final" cell product, or other intermediate products obtained during the biological fluid processing.

As will be seen in the Figures and described in greater detail below, the disposable fluid processing circuit includes tubing that defines flow paths throughout the circuit, as well as access sites for sterile or other connection to containers of processing solutions, such as wash solutions, treating agents, and sources of the biological fluid. As will be apparent from the disclosure herein, a single source container 102 or multiple source containers (102a, 102b, 102c, as shown in FIG. 2) may be attached in sterile fashion to circuit 100.

Figure 2:
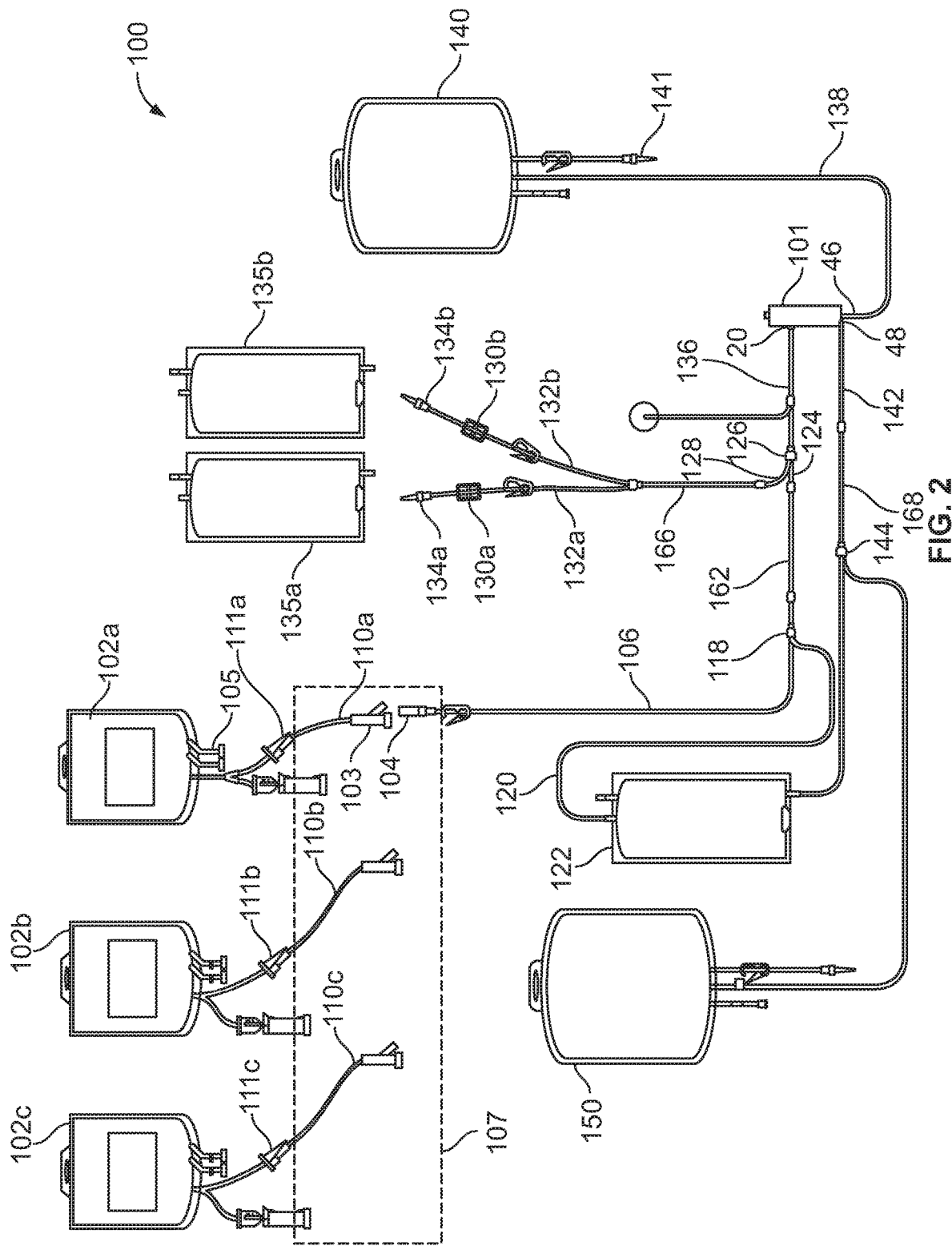
FIG. 2 is a schematic view of another embodiment of disposable fluid circuit with multiple source containers for use in the systems and methods described herein.

As shown in FIGS. 1 and 2, the tubing of circuit 100 includes spaced tubing segments identified by reference numerals 162, 166, 168. The tubing segments are provided for mating engagement with the peristaltic pumps of the reusable hardware apparatus 200 discussed below. The containers and the plastic tubing are made of conventional medical grade plastic that can be sterilized by sterilization techniques commonly used in the medical field, such as, but not limited to, radiation or autoclaving. Plastic materials useful in the manufacture of containers and tubing in the circuits disclosed herein include plasticized polyvinyl chloride. Other useful materials include acrylics. In addition, certain polyolefins may also be used.

The biological fluid, such as a biological cell suspension, to be processed is typically provided in a source container 102, shown in FIG. 1 as (initially) not connected to the disposable set. As noted above and shown in FIG. 2, one or more source container(s) (102a, 102b, 102c) may be attached (in sterile fashion) at the time of use. Source container(s) 102 may include one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source containers(s) 102. In accordance with the methods and systems described herein and as previously noted, multiple source containers 102a, 102b, 102c, etc., may be provided for the processing of larger volumes of the biological fluid. While three (3) source containers are shown, it will be appreciated that more (or less) than three source containers may be processed in the course of a processing procedure.

As shown in FIG. 2, where multiple source containers 102a, 102b, and 102c are to be processed, circuit 100 may optionally include a manifold 107 (shown in dashed lines), or other branched member 109 that receives and communicates with individual source lines 110a, 110b, and 110c. Manifold 107 or other branched member is in fluid communication with primary source line 106, as shown. Flow through source line 110 (FIG. 1), or multiple, individual source lines 110a, 110b, and 110c may be manually controlled by roller, slide clamp or Roberts-type clamps 111 (FIG. 1) or 111a, 111b, and 111c (FIG. 2).

With further reference to FIGS. 1 and 2, tubing (source line) 106 is connected to downstream branched-connector 118. Branched-connector 118 communicates with tubing 106 and tubing 120, which provides a fluid flow path from "in-process" container 122, described in greater detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIGS. 1 and 2, one or more container(s) 135a/135b of priming/wash or other processing/treating solution may be attached to fluid circuit 100. As further shown in FIGS. 1 and 2, tubing 132a (defining a flow path) preferably includes and terminates in an access site such as spike connector 134a. Access sites 134a/134b are provided to establish flow communication with containers 135a/135b (shown in FIGS. 1 and 2) of a priming/wash fluid, such as saline or other solution. More preferably, flow communication between tubing 132a and a container of priming/wash solution may be achieved by sterile connection device, such as, but not limited to, the previously mentioned Terumo SCD IIB. The priming/wash solution flows from the wash fluid source through tubing segment 132a, and then passes through tubing 128 to the input of the branched-connector 126 described above. The priming/wash solution then flows through tubing segment 124 and source line 106 to one or more source containers (See FIGS. 1 and 2).

It should be noted that access site 134b may be used to establish fluid communication with additional containers of priming/wash solution (as shown) or other solutions and/or agents.

As further shown in FIGS. 1 and 2, tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated herein by reference, U.S. Provisional Patent Application Ser. No. 61/451,903, and PCT/US2012/028522, also previously incorporated herein by reference. In an alternative embodiment, separator 101 may utilize a different separation principle. For example, separator 101 may be a centrifuge.

As seen in FIGS. 1 and 2, spinning membrane separator 101 has at least two outlet ports. Outlet 46 of separator 101 receives the separated filtrate (e.g., separated biological cells) and is connected to tubing 138, which defines a flow path to filtrate/cell container 140. The filtrate/cell container may further include connection port 141 for sampling the contents within the filtrate/cell container 140.

Separation device 101 preferably includes a second outlet 48 that is connected to tubing segment 142 for directing the retentate to branched-connector 144, which branches into and defines a flow path to one or more in-process containers 122 and/or a flow path to a retentate container 150.

FIG. 3 shows the front panel 201 of reusable hardware processing apparatus 200. Apparatus 200 may be of compact size suitable for placement on a table top of a lab bench and adapted for easy transport. Alternatively, apparatus 200 may be supported by a pedestal that can be wheeled to its desired location. In any event, as shown in FIG. 3, apparatus 200 includes a plurality of peristaltic pumps, such as pumps 202, 204, and 206 on front panel 201. Pump segments 166, 162, and 168 of the disposable fluid circuit (described above) are selectively associated with peristaltic pumps 202, 204, and 206. The peristaltic pumps articulate with the fluid sets of FIGS. 1 and 2 at the pump segments identified by reference numerals 162, 166, 168 and advance the priming solution and ultimately the cell suspension or other fluid within the disposable set, as will be understood by those of skill in the art. Apparatus 200 also includes clamps 210, 212, 214, 216, and 218. Clamps 210, 212, 214, 216, and 218 are used to control the flow of the cell suspension through different segments of the disposable set.

Apparatus 200 also includes several sensors to measure various conditions. The output of the sensors is utilized by device 200 to operate one or more processing or wash cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces. In accordance with the system priming described herein, air detector 238 may be used to generate an alert/alarm which may indicate incomplete priming or insufficient processing, requiring some correction and/or intervention by the operator. This is discussed in further detail below.

Apparatus 200 includes weight scales 240, 242, 244, 246, 250, and 252 from which the cell container, in-process container, source container, and any additional container(s) (e.g., wash or priming solution container, retentate container, filtrate container, source container) may depend and be weighed. The weights of the containers are monitored by weight sensors and recorded during a washing or other procedure, including during the priming steps described herein. Where multiple source containers are to be processed, some of the source containers may be suspended from a standard I.V. pole or the like (in which case scale measurements would not be taken but pump strokes counted). From measurements of the weight sensors, the device, under the direction of the controller, determines whether each container is empty, partially full or full, and controls the components of apparatus 200, such as the peristaltic pumps and clamps 210, 212, 214, 216, 218, 220, 222, and 224. In accordance with the present disclosure, weight sensors may provide volumes of biological fluid in source containers 102 (102a, 102b, 102c, etc.) and monitor the changing volume of priming/wash solutions in containers 135 (a and/or b) during priming, discussed in greater detail below. Alternatively, additional source containers 102 may be suspended from IV poles proximally located to apparatus 200.

Apparatus 200 includes at least one drive unit or "spinner" 248 (FIG. 3), which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
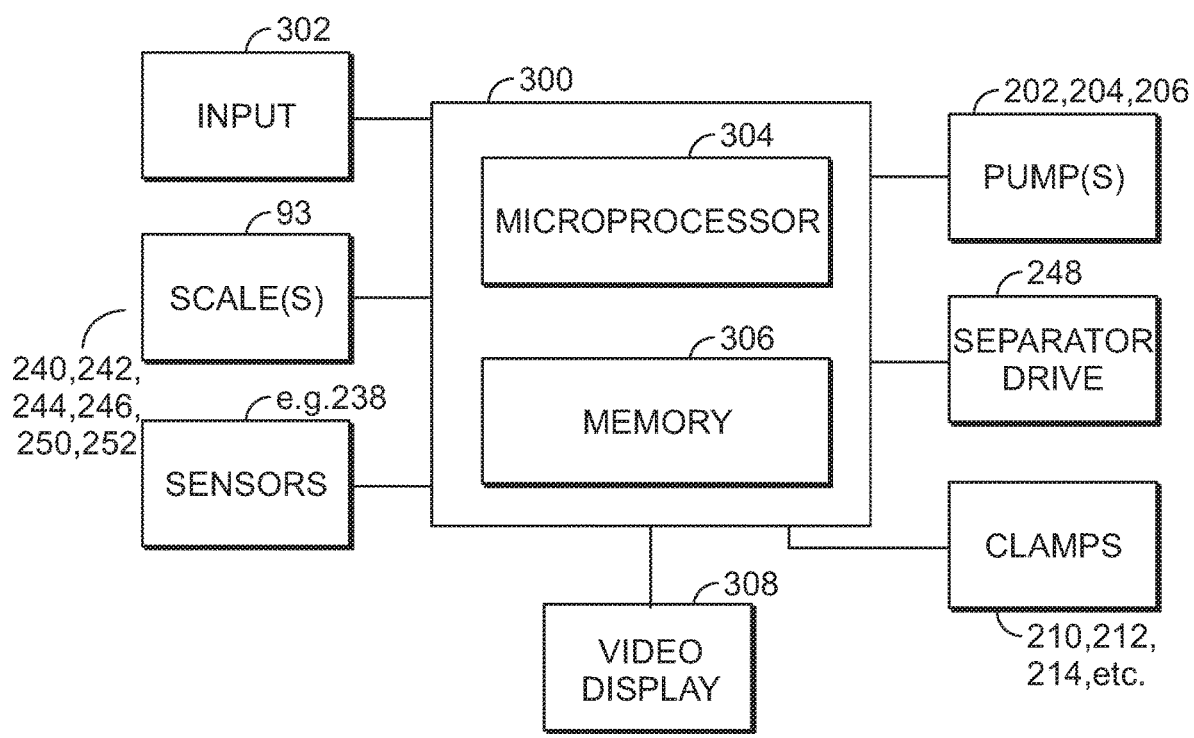
FIG. 5 is a schematic view of the control circuitry, including the controller, of the device of FIG. 3.

FIG. 5 is a schematic view of the control unit or "controller" 300 included in device 200 of the present disclosure. The controller 300 may include a microprocessor 304 (which may include multiple physical and/or virtual processors). According to other embodiments, the controller 300 may include one or more electrical circuits designed to carry out the actions described herein. In an embodiment, controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304 may cause the microprocessors 304 to carry out one or more actions as described herein.

As is also illustrated in FIG. 5, controller 300 may be coupled to one or more of the structures described above, for example, to receive information (e.g., in the form of signals) from these structures or to provide commands (e.g., in the form of signals) to these structures to control the operation of the structures. As illustrated in FIG. 5, the controller 300 may be coupled to the scales 240, 242, 244, 246, 250, 252, etc., (seen in FIG. 3) that hold solution containers or that are provided to collect blood components, the sensors associated with device 200, clamps washed, concentrated, or otherwise processed, and the at least one input 302 to receive information from those devices. Additionally, the controller 300 may be coupled to pumps 202, 204, and 206 and the separator drive unit 248 to provide commands to those devices and to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel of the device 10, the video display 308 also being coupled to the controller 300. The assembly of the input/touch screen 302 and video display 308 may be one of the afore-mentioned structures to which the controller 300 is coupled from which the controller 300 receives information and to which the controller 300 provides commands.

Figure 6:
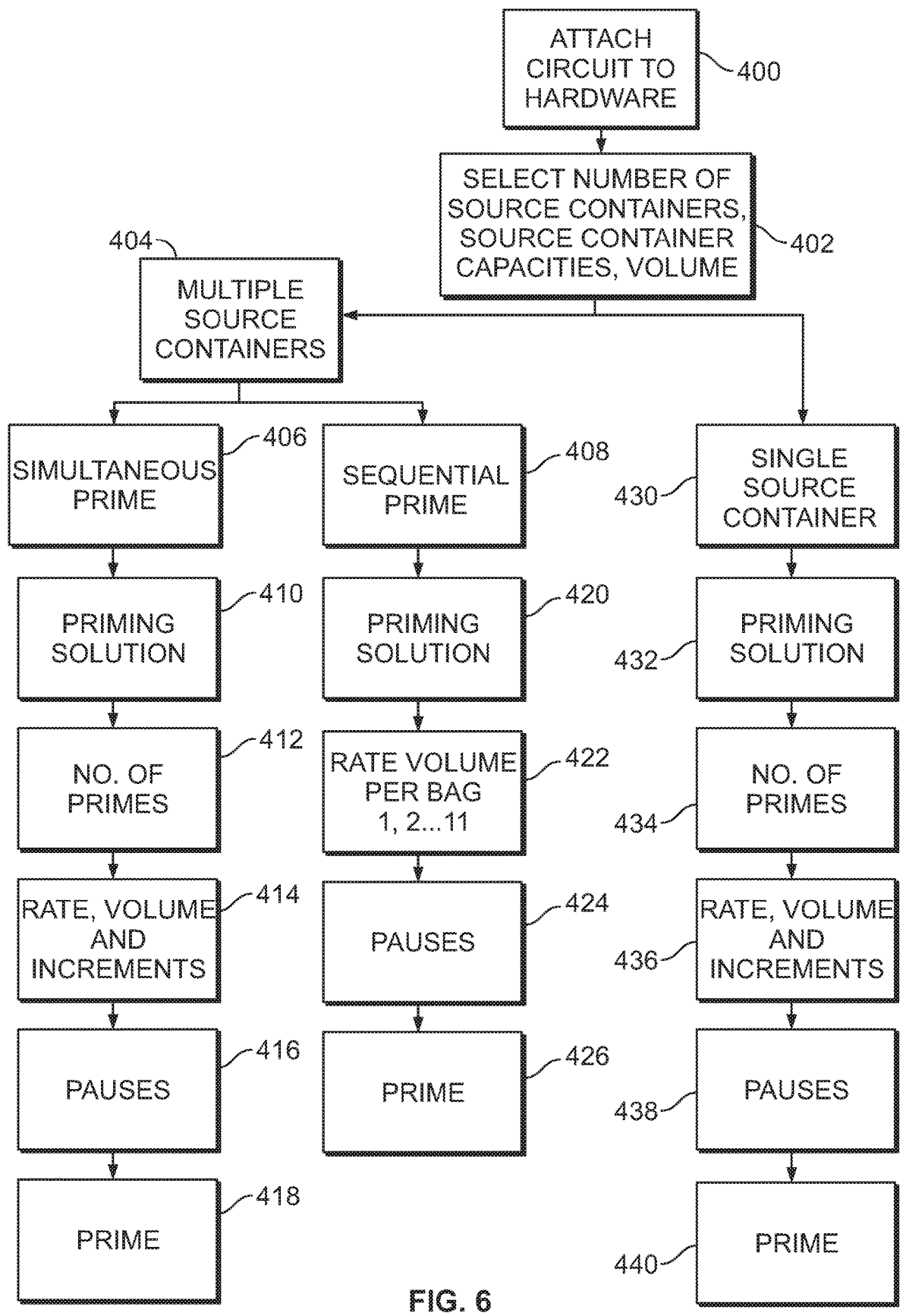
FIG. 6 is a flow chart setting forth steps of the method of priming disclosed herein.

Prior to introduction of biological cells into separator 101, the system (under the direction of controller 300) may initiate priming of the flow paths of the circuit. The circuit may be primed with a priming solution, such as wash solution, suspended from one more hangers/weight scales of the reusable device 200. Prior to priming, the operator may enter a series of instructions to configure the priming of at least a portion of the fluid circuit based on the number of source containers, the total volume of source liquid to be processed, the source bag(s) capacity(ies), the number of "primes," the duration and interval of "pauses," the flow rate of the priming solution, etc. For example, after fluid circuit 100 has been mounted onto hardware 200 (see block 400 of FIG. 6), the system has conducted the necessary checks, and one or more source containers 102 (102a, 102b, etc.) have been attached, as shown in FIG. 6, the operator may select (block 402) whether one source container of biological fluid is to be processed (block 430) or multiple containers of biological fluid are to be processed (block 404). The operator may also enter the total volume of source liquid to be processed, the capacity of the source containers, the volume of source liquid in each of the multiple source containers, and the composition of the source liquid. If multiple containers are to be processed, the operator may enter the number of source containers to be processed (and total volume) and may further select whether such multiple source containers will be primed sequentially (i.e., bag 102a, followed by bag 102b, followed by bag 102c, etc., as shown in block 408) or simultaneously, as shown in block 406.

As further shown in FIG. 6, the operator may also select the priming solution from among two or more solutions (blocks 410 and 420), the number of "primes" (block 412), the volume of priming solution and the flow rates of the priming solution. In addition, the operator may also introduce a "pause" between selected primes as well as the duration of such pause (blocks 416 and 424). Thus, for example, where sequential priming has been selected (block 408) the operator may introduce pauses of selected duration between priming of container 102a, 102b, 102c, etc. Introducing pauses of selected duration allows the operator to mix (e.g., manually) the priming solution with the biological fluid source and reduce the possibility of "shock" to the cells and allow for osmotic balancing. Where simultaneous priming of multiple source containers and their source lines is selected, the operator may introduce pauses between a plurality of simultaneous "primes" to allow for mixing of the priming solution with the biological fluid in each of the multiple source containers. After the pause period, additional priming solution may be simultaneously delivered to each of the multiple source containers, followed by another pause period to allow for additional mixing. These alternating prime and pause cycles may be repeated as necessary.

Where a single container of source solution is to be processed (block 430), the operator, after selecting the priming solution (block 432) may likewise select the number of "primes" and further select a flow rate and volume for each of the primes (block 436). Multiple primes may be desired to allow for osmotic balancing to occur. As with the priming of multiple source containers, the operator may introduce pauses of selected duration between the multiple "primes" to allow for mixing of the biological fluid with the priming solution.

The steps described above are not limited to the specific order presented. For example, selection of the priming solution may be made prior to selecting whether to prime multiple source lines and containers sequentially or simultaneously.

Once the priming instructions have been entered, the operator may initiate the priming cycle (blocks 418, 426, 440) whereby controller 300 effects the necessary opening and closing of clamps 210, 212, 214, activation and directional rotation of pumps (202 and 204), pump rotations, including the rate of rotations to provide the desired flow rate of priming solution, number of rotations to provide the desired volume of delivered priming solution, and starts and stops of pump 202 and 204 to effect the desired pauses and multiple "primes," in accordance with the entered input by the operator. Thus, priming can proceed without significant operator intervention and in accordance with sequences configured by the operator. The operator may manually open or close clamps 111, 111a-111c as necessary to allow flow of priming solution to the one or more source containers.

In accordance with the present disclosure, the methods and systems described herein may include an alert/alarm condition which may be indicative of incomplete or ineffective priming. Air detector 238 may be programmed to detect the presence of air at a given point in time during cell processing. For example, if the volume of source liquid and/or the number of source containers has been entered incorrectly (e.g., fewer than the actual number of containers or less than the actual volume entered), air detector 238 may detect the presence of air sooner than expected. This may generate an alert/alarm requiring the operator to check whether the data entered matches the actual source volume, number of source containers, or that connections to the source containers have been properly made and confirm whether or not all source lines and source containers have been effectively primed, processed, or rinsed.

The description provided above is intended for illustrative purposes, and is not intended to limit the scope of the disclosure to any particular method, system, apparatus or device described herein.

The invention claimed is:

1. An automated system for the processing of biological fluid comprising:
   a. a reusable hardware unit comprising at least a separation device drive unit for receiving a single separation device, a plurality of pumps, and a controller;
   b. a disposable fluid circuit mountable on said reusable hardware unit, said disposable fluid circuit including tubing defining multiple flow paths between a container of a priming solution in openable fluid communication with multiple suspended flexible containers of a source liquid comprising the biological fluid;

wherein said controller is configured to control flow of said priming solution by a number and sequence of deliveries of said priming solution communicating with said multiple source containers through said multiple flow paths based on at least the total number of said multiple source containers of the biological fluid and wherein said controller is further configured to (i) allow for selection of either sequential delivery or simultaneous delivery of said priming solution to said multiple flow paths and said multiple source containers and to (ii) effect a pause in the flow of said priming solution of the selected delivery of said priming solution to allow for mixing of the priming solution with the source liquid in each of said multiple source containers, and to resume the selective delivery of said priming solution after the pause.

2. The system of claim 1 wherein said controller is configured to determine the volume of said priming solution to be delivered to each of said multiple source containers.

3. The system of claim 2 wherein said controller is configured to incrementally deliver said priming solution.

4. The system of claim 3 wherein said controller is configured to pause said incremental delivery of said priming solution, wherein said pause is of a predetermined duration.

5. The system of claim 1 wherein said controller is configured to deliver said priming solution at variable flow rates.

6. The system of claim 1 wherein said disposable fluid circuit includes a manifold providing fluid communication with said multiple source containers.

7. The system of claim 1 further comprising a sensor for detecting the presence of air within said fluid circuit and said controller is configured to effect re-priming of at least a portion of said disposable fluid circuit in response to said detecting.

8. The system of claim 1 wherein said controller is configured to effect delivery of said priming solution to each of said multiple source containers of the biological fluid in variable volumes.

9. The system of claim 1 wherein said controller is configured to effect delivery of said priming solution to each of said multiple source containers of the biological fluid incrementally.

10. The system of claim 1 wherein said controller is configured to effect delivery of said priming solution to each of said multiple source containers of the biological fluid at varying flow rates.

11. The system of claim 1 wherein said disposable fluid circuit includes a separation device comprising a spinning membrane separator.

12. The system of claim 1 wherein the controller is further configured to control the number and sequence of selective deliveries of said priming solution communicating with said multiple source containers through said multiple flow paths based on one or more of i) the source container(s) capacity(ies), ii) the number of deliveries of said priming solution, iii) the duration and interval of pauses, iv) the flow rate of the priming solution, and v) the composition of the source liquid.

13. The system of claim 1 comprising an alert and/or alarm condition that indicates incomplete or ineffective priming wherein said alert and/or alarm is triggered when the number of multiple source containers has been entered incorrectly.

* * * * *